United States Patent [19]

Spencer

[11] Patent Number: 4,801,295

[45] Date of Patent: * Jan. 31, 1989

[54] DISPOSABLE HYPODERMIC SYRINGE AND NEEDLE COMBINATION HAVING RETRACTABLE, ACCIDENT PREVENTING SHEATH

[76] Inventor: Treesa A. Spencer, 1882 Winnebago, El Toro, Calif. 92630

[ * ] Notice: The portion of the term of this patent subsequent to Oct. 27, 2004 has been disclaimed.

[21] Appl. No.: 112,538

[22] Filed: Oct. 22, 1987

Related U.S. Application Data

[63] Continuation-in-part of Ser. No. 866,151, May 22, 1986, Pat. No. 4,702,738.

[51] Int. Cl.$^4$ ............................................. A61M 5/32
[52] U.S. Cl. .................................... 604/198; 604/199; 604/263
[58] Field of Search ............... 604/198, 199, 187, 192, 604/263

[56] References Cited

U.S. PATENT DOCUMENTS 3,874,383  4/1975  Glowacki ..................... 604/199X
4,702,738 10/1987  Spencer ............................. 604/198

Primary Examiner—John D. Yasko
Attorney, Agent, or Firm—Klein & Szekeres

[57] ABSTRACT

A disposable combination of a hypodermic syringe and needle has a sheath movably mounted on the syringe barrel to normally occupy a first position wherein the sheath extends to cover and protect the needle. In a second position of the sheath, relative to the barrel and needle, the needle is at least partially exposed. In a third position of the sheath, which is used for disposal of the syringe and needle combination, the needle is again covered by the sheath and preferably the sheath is irreversibly locked whereby abuse or misuse of the syringe and needle combination is substantially prevented. The sheath is made from a plastic material, such as styrene butadiene or acrylic styrene copolymer, which has a deflection temperature below the temperature required for heat sterilizing syringes. Consequently, upon attempted sterilization by heat, the sheath melts, thereby further rendering the combination usable only once.

10 Claims, 4 Drawing Sheets

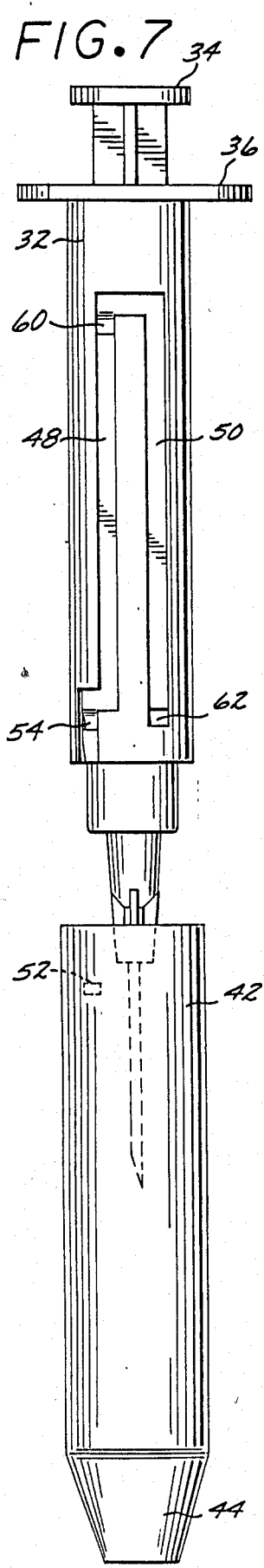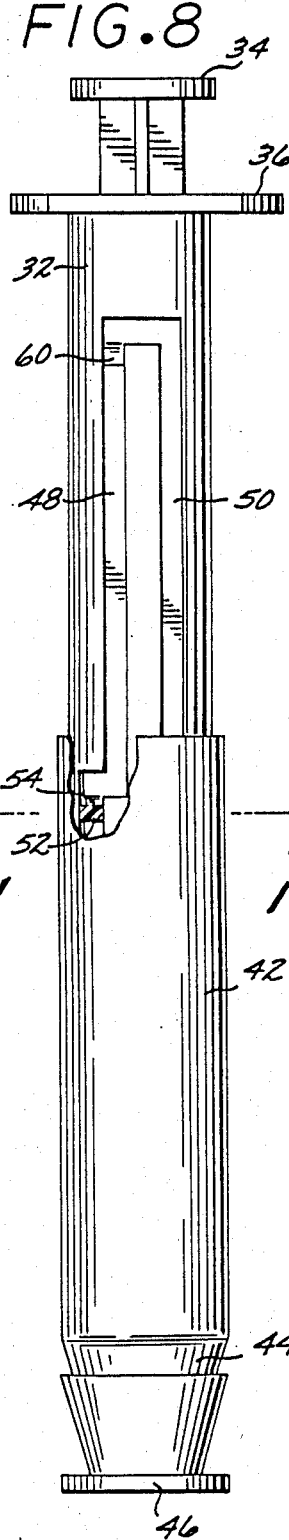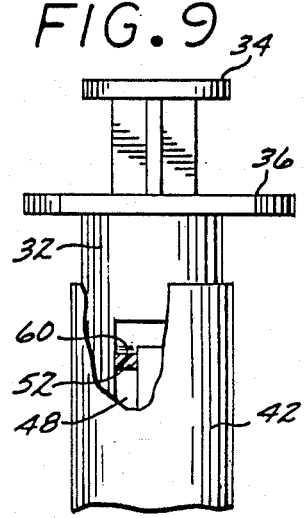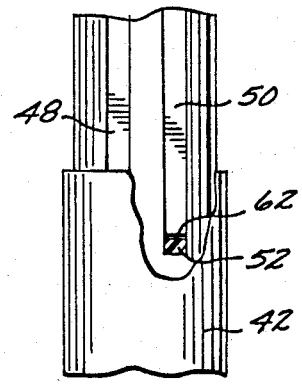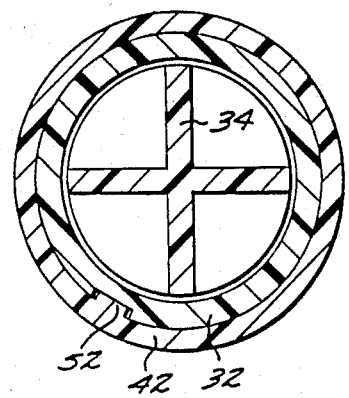

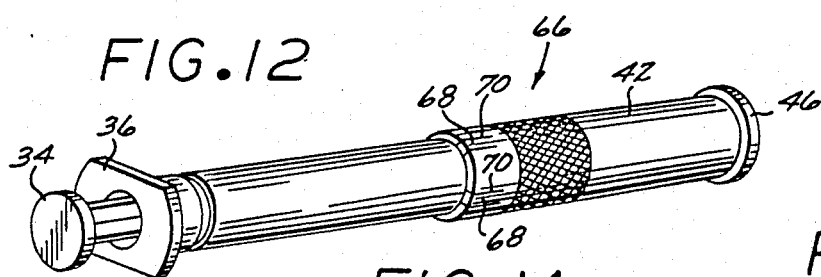
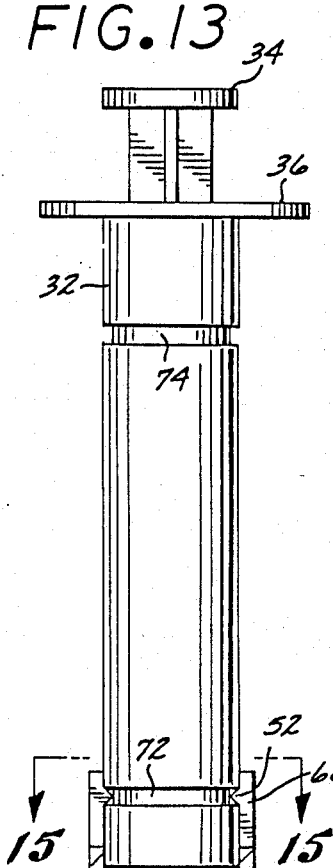
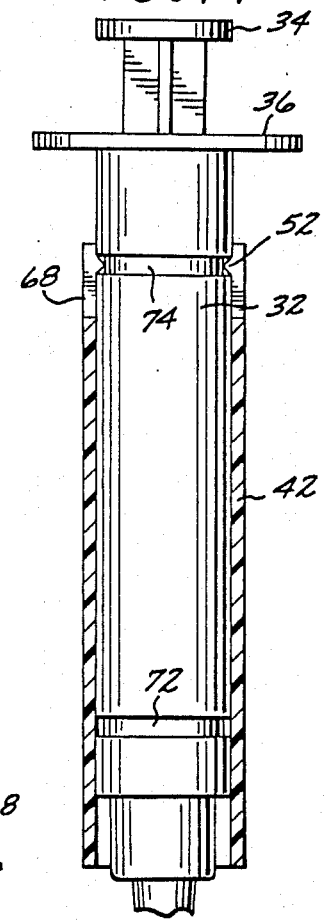
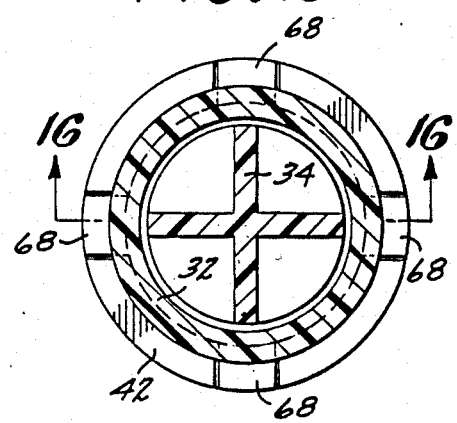
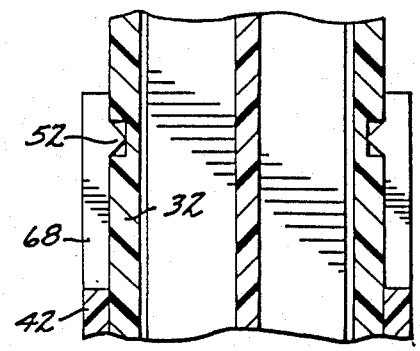
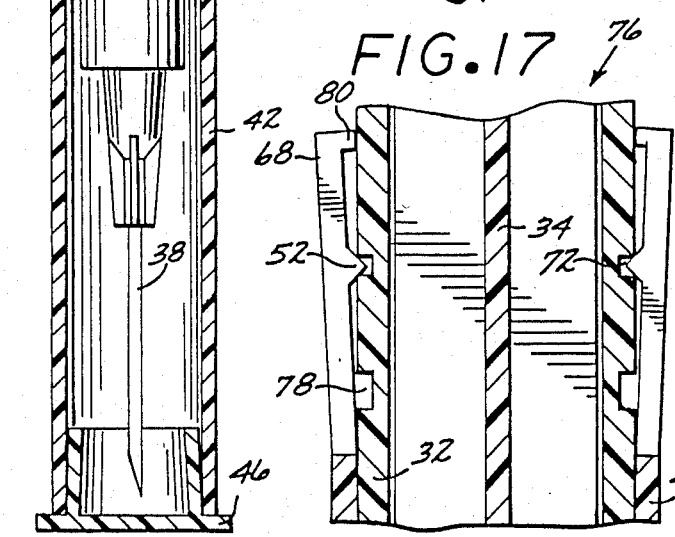
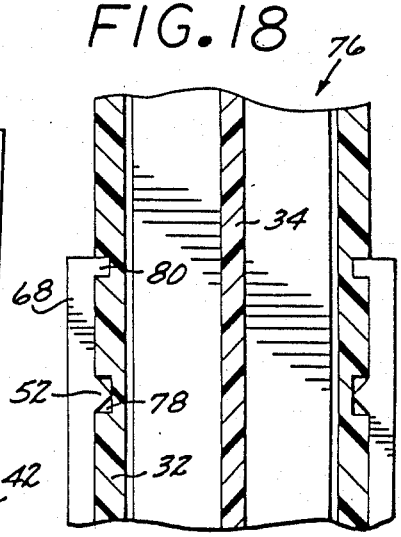

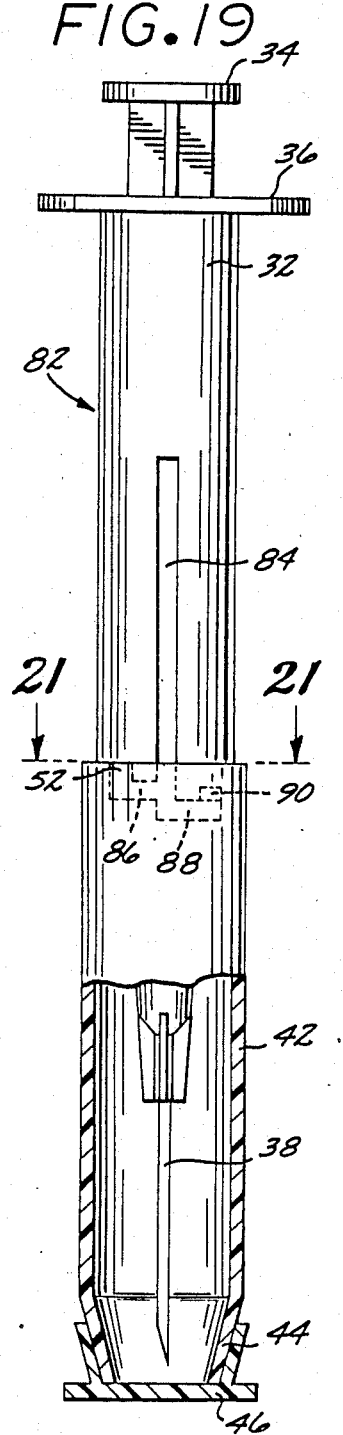
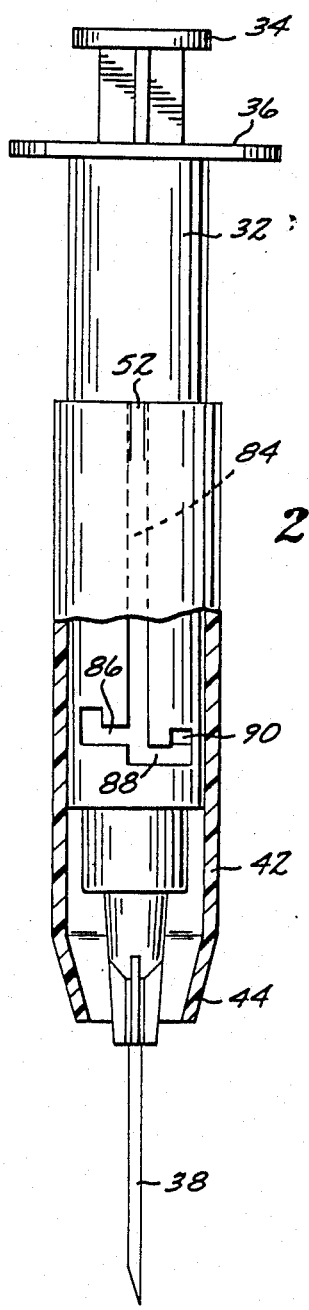
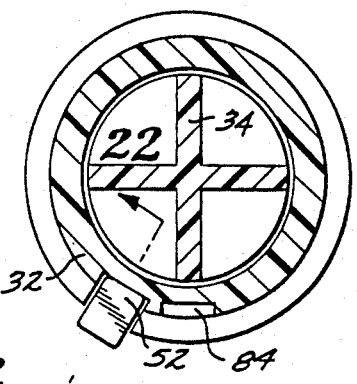
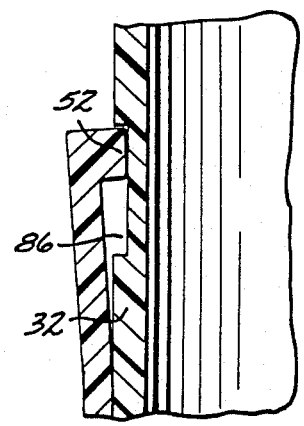
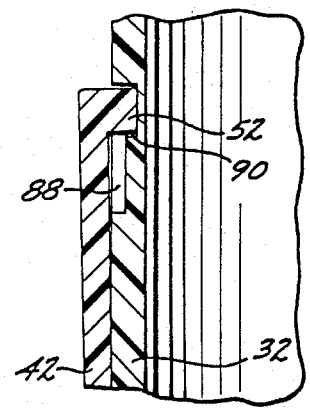
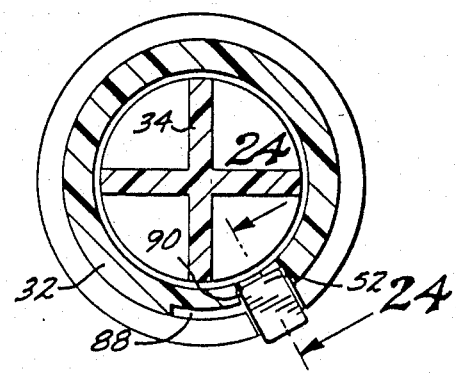

DISPOSABLE HYPODERMIC SYRINGE AND NEEDLE COMBINATION HAVING RETRACTABLE, ACCIDENT PREVENTING SHEATH

BACKGROUND OF THE INVENTION

1. Cross-Reference to Related Application

The present application is a continuation-in-part of my application Ser. No. 866,151, filed on May 22, 1986, now U.S. Pat. No. 4,702,738.

2. Field of the Invention

The present invention is in the field of hypodermic syringes and needles. More particularly, the present invention is directed to a disposable hypodermic syringe and needle combination which has a retractable sheath to prevent accidents and abuse of the syringe and needle combination.

3. Brief Description of the Prior Art

Disposable hypodermic syringes and needles have been known in the art for a long time.

Hypodermic syringes and needles are often used for administering medication to patients suffering from infectious diseases. Therefore, it has been considered of great importance in the art to avoid accidents where doctors, nurses, or other persons are wounded by used hypodermic needles. Presently, the safe disposal of used syringes and needles is considered a serious problem in the art, particularly in light of the recent spread of acquired immunodeficiency syndrome (AIDS), and of the widespread abuse of syringes and needles by addicts for administering illicit drugs.

In order to solve or ameliorate the foregoing problems, the prior art has provided rigid, puncture resistant disposable plastic containers into which doctors or nurses are expected to deposit disposable hypodermic syringes and needles immediately after their use. The containers, filled with the discarded syringes and needles, are then sealed and eventually disposed of. The disposal is ideally conducted in a manner which does not permit access to unauthorized persons desiring to obtain the syringes and needles for illegal or like abusive purposes. In spite of the foregoing and other precautions, accidents still occur with used hypodermic needles, sometimes with tragic consequences. Moreover, discarded syringes and needles are still often misappropriated for illegal, or drug abuse, purposes.

The foregoing problems remain especially acute in connection with syringes and needles used by paramedics, because paramedics often are unable to carry the specialized plastic containers required for safe disposal. Moreover, personnel working in housekeeping duties in hospitals presently are still often exposed to improperly discarded hypodermic syringes and needles. The present invention is designed to solve or substantially ameliorate the above-described problems.

SUMMARY OF THE INVENTION

It is an object of the present invention to provide a disposable hypodermic syringe and needle combination wherein the needle is protected before and after use, to prevent accidents involving the used needle.

It is another object of the present invention to provide a disposable hypodermic syringe and needle combination wherein the needle is protected before use, and wherein the needle is permanently and irreversibly concealed after use so as to prevent abuse by users of illicit drugs.

The foregoing and other objects and advantages are attained by a hypodermic syringe and needle combination having a sheath mounted to the barrel in a first position wherein the sheath extends and conceals the needle. The sheath is movable on the barrel to occupy a second position wherein the needle is at least partially exposed. The needle and syringe combination is normally used to fill the syringe with medication and inject it into the patient in the second position of the sheath. The sheath is also movable to a third position on the barrel wherein the sheath again conceals the needle. The sheath is preferably irreversibly locked into the third position for disposal so that the combination cannot be retrieved and used for illegal or unauthorized purposes.

In accordance with another feature of the invention, the sheath is made from a plastic material which softens and loses its structural integrity at temperatures below the autoclaving temperatures required for sterilizing items in medical practice. Consequently, the needle and syringe combination is destroyed upon attempted sterilization in an autoclave, because the sheath "melts" and renders the combination unusable. This feature ensures that the combination is used only once.

The features of the present invention can be best understood together with further objects and advantages by reference to the following description, taken in connection with the accompanying drawings, wherein like numerals indicate like parts.

BRIEF DESCRIPTION OF THE DRAWINGS

FIG. 7 is a partially exploded side view of the first preferred embodiment;

FIG. 8 is a side view of the first preferred embodiment with a portion of the protective sheath broken away, the view showing the protective sheath in its extended position covering the needle;

FIG. 9 is a partial side view of the first preferred embodiment, with a portion of the protective sheath broken away, the view showing the protective sheath in its retracted position wherein the needle is exposed;

FIG. 10 is another partial side view of the first preferred embodimett, with a portion of the protective sheath broken away, the view showing the protective sheath in its extended locked position covering the needle;

FIG. 11 is a cross-sectional view, the cross-section being taken on lines 11,11 of FIG. 8;

FIG. 12 is a perspective view of a second preferred embodiment of the hypodermic syringe and needle combination of the present invention, the view showing a protective sheath extended to cover the needle;

FIG. 13 is a side view of the second preferred embodiment, partly in cross-section, the side view showing the protective sheath extended to cover the needle;

FIG. 14 is a partial side view of the second preferred embodiment, partly in cross-section, the view showing the protective sheath retracted to expose the needle;

FIG. 15 is a cross-sectional view of the second preferred embodiment, the cross-section being taken on lines 15,15 of FIG. 13;

FIG. 16 is a partial cross-sectional view of the second preferred embodiment, the cross-section being taken on lines 16,16 of FIG. 15;

FIG. 17 is a partial cross-sectional view of a third preferred embodiment of the hypodermic syringe and needle combination of the present invention, the view corresponding to an extended position of a protective sheath to cover the needle;

FIG. 18 is another partial cross-sectional view of the third preferred embodiment, the view corresponding to an extended and irreversibly locked position of the protective sheath to cover the needle;

FIG. 19 is a side view, partly in cross-section, of a fourth preferred embodiment of the hypodermic syringe and needle combination of the present invention, the view showing a protective sheath extended to cover the needle;

FIG. 20 is another side view, partly in cross-section, of the fourth preferred embodiment, the view showing a protective sheath retracted to cover the needle;

FIG. 21 is a cross-sectional view taken on lines 21,21 of FIG. 19;

FIG. 22 is a cross-sectional view taken on lines 22,22 of FIG. 21, the view corresponding to an extended position of the protective sheath to cover the needle;

FIG. 23 is another cross-sectional view of the fourth preferred embodiment, the view corresponding to a locked position of the protective sheath to cover the needle, and FIG. 24 is a cross-sectional view taken on lines 24,24 of FIG. 23.

DESCRIPTION OF THE PREFERRED EMBODIMENTS

Figure 1:
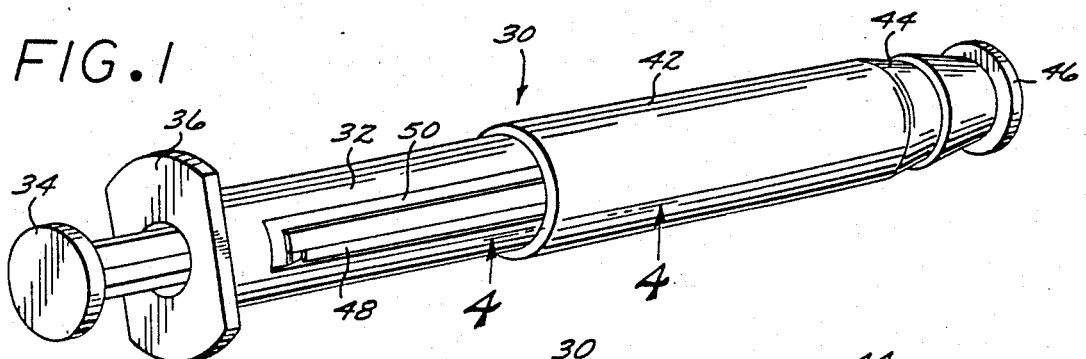
FIG. 1 is a perspective view of a first preferred embodiment of the hypodermic syringe and needle combination of the present invention, the view showing a protective sheath extended to cover and conceal the needle.

The following specification taken in conjunction with the drawings sets forth the preferred embodiments of the present invention. The embodiments of the invention disclosed herein are the best modes contemplated by the inventor for carrying out her invention in a commercial environment, although it should be understood that several modifications can be accomplished within the scope of the present invention.

Referring now to FIGS. 1 through 11 of the appended drawings, a first preferred embodiment 30 of the hypodermic syringe and needle combination of the present invention is disclosed. The first preferred embodiment 30 includes a syringe barrel 32 and a plunger 34 mounted into the barrel 32 at its first end 36. A hypodermic needle 38 is mounted in a conventional manner to the second end 40 of the barrel 32.

As an important novel feature, a sheath 42 is mounted to the barrel 32 at the same end 40 of the barrel 32 where the needle 38 is mounted. As is best shown on the perspective view of FIG. 1, in its normal or first position, the sheath 42 is disposed to conceal and cover the needle 38. The combination of the first preferred embodiment 30 is assembled during manufacture, and is kept, during shipping, storage, and preliminary preparation for administration of medication (not shown) to a patient (not shown), with the sheath 42 in its extended first position. To insure sterility, the sheath 42 is preferably sealed to the barrel with an airtight flexible plastic wrap (not shown) The flexible wrap (not shown) also serves as a tamper indicator.

The end 44 of the sheath 42, which is remote from the barrel 32, is tapered in the first preferred embodiment 30, and bears a friction fitted plastic cap or cover 46. The cap or cover 46 is shown on FIGS. 1 and 8.

As is apparent from FIGS. 1 through 11, the sheath 42 can be moved on the barrel 32 to expose the needle 38 when it is desired to fill the barrel 32 with medication (not shown) and administer the medication (not shown) to a patient (not shown). More particularly, the sheath 42 is locked in its first position to the barrel 32, but can be dislodged from the first position to be moved to a second position to expose the needle 38. The second position is shown on FIG. 2. Still a third position of the sheath 42 relative to the barrel 32 and needle 38 is shown on FIG. 3. In the third position, into which the sheath 42 is placed for disposal of the hypodermic syringe and needle combination 30, the sheath 42 is substantially irreversibly locked to cover and conceal the needle 38. Consequently, in its "disposal state", the hypodermic syringe and needle combination 30 cannot be accidentally reused, and the needle 38 is prevented from accidentally wounding someone, thereby potentially spreading dangerous infectious disease. As an added safety feature, after the sheath 42 is locked into the third position shown on FIG. 3, but before final discarding, the cap or cover 46 is preferably refitted to the sheath 42.

The above-described functions of the preferred embodiment 30 are accomplished by the structure illustrated in FIGS. 1–11. More particularly, the surface of the barrel 32 includes a channel or groove having two interconnected elongated parallel portions, which respectively bear the reference numerals 48 and 50 on the drawing Figures. The interior surface of the sheath 42 includes a protrusion or boss 52 which fits into and is guided in the channels 48 and 50. The channels or grooves 48 and 50 are approximately 0.008" to 0.012" deep.

Figure 4:
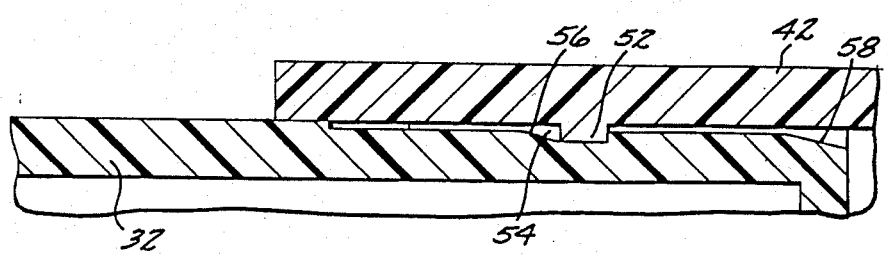
FIG. 4 is a cross-sectional view taken on lines 4,4 of FIG. 1.

The partial cross-sectional view of FIG. 4 shows the boss 52 placed into the channel 48 in the first position of the sheath 42 (in which the combination 30 is normally kept prior to use). In order to reversibly lock the sheath 42 in this position the guide channel 48 has a depression or cavity 54 in a location corresponding to the location of the boss 52 in the first position of the sheath 42. The cavity 54 includes a camming surface 56 comprising a slope or a radius, which permits the substantially square-shaped boss 52 to ride out of the cavity 54 in one direction only. FIG. 4 also shows a slope or camming surface 58 at the end 40 of the barrel 32, which permits the initial mounting of the sheath 42 on the barrel 32 without serious interference by the boss 52. FIG. 7 shows well the interconnecting guide channels 48 and 50, and also shows the sheath 42 before it is initially mounted to the barrel 32. The configuration of the cavity 54 shown on FIG. 4 renders it substantially impossible to remove the sheath 42 from the barrel 32 without breaking or damaging the boss 52 and thereby the entire combination 30. In addition to FIG. 4, FIGS.

8 and 11 also show the sheath 42 mounted to the barrel 32 in the first position wherein the boss 52 engages the cavity 54 in the guide channel 48.

Figure 2:
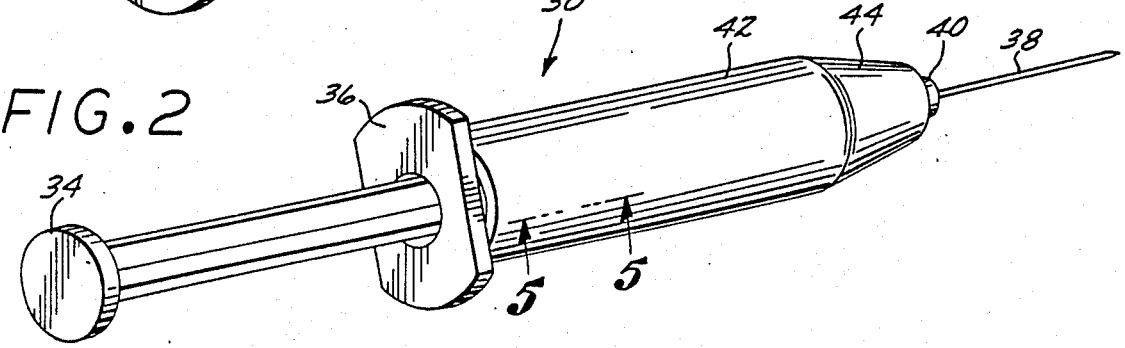
FIG. 2 is another perspective view of the first preferred embodiment, the view showing a protective sheath retracted, thereby exposing the needle.
Figure 3:
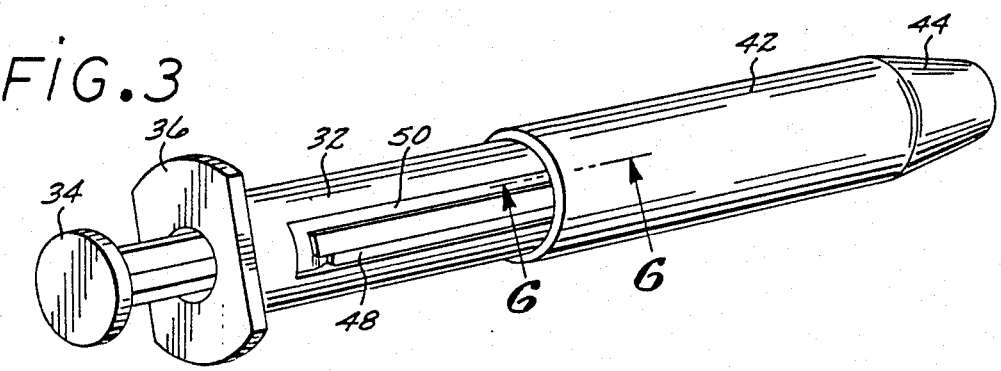
FIG. 3 is still another perspective view of the first preferred embodiment, the view showing the protective sheath again extended and locked into position after the combination has been used.
Figure 5:
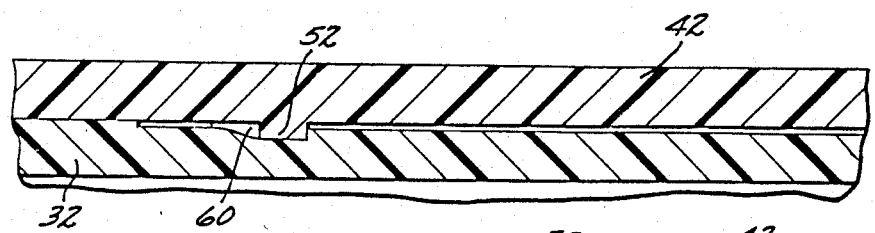
FIG. 5 is a cross-sectional view taken on lines 5,5 of FIG. 2.

FIGS. 2, 5, and 9 indicate the second position of the sheath 42 relative to the barrel 32. In this position, the boss 52 of the sheath 42 engages a second depression or cavity 60, which is located almost at the upper end of the guide channel 48. The shape or configuration of the second cavity 60 is similar to that of the first cavity 54, so that the boss 52 can ride out of the second cavity 60 in the upwardly direction only.

Figure 6:
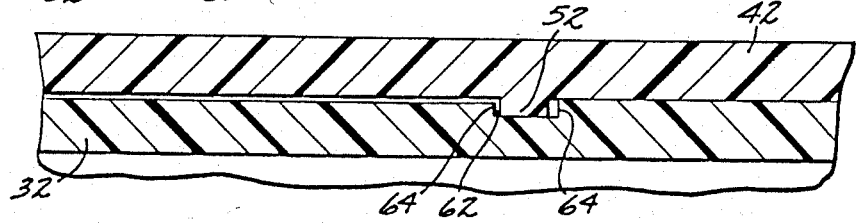
FIG. 6 is a cross-sectional view taken on lines 6,6 of FIG. 3.

FIGS. 6 and 10 show the boss 52 of the sheath 42 engaging, in the third position of the sheath 42, a third depression or cavity 62 located substantially at the lower end of the guide channel 50. The third cavity 62 has no slope or camming surface; rather it has straight walls 64 designed to capture the boss 52, and thereby irreversibly lock the sheath 42 in the position concealing the needle 38. It is apparent from an inspection of FIG. 6 that the sheath 42 can be moved out of the third position only by breaking or substantially damaging the boss 52.

All components of the above-described combination 30, with the exception of the metal body of the needle 38, can be manufactured by injection molding from plastic materials of the type ordinarily used for the manufacture of hypodermic syringes. Medical grade polypropylene, for example, is suitable material for the manufacture of the syringe.

The sheath 42, however, can be made of a lower non-medical grade of plastic because it does not come into contact with medication. In fact, as an additional novel feature of the present invention, the sheath 42 is made of a plastic material which melts at substantially lower temperature than the medical grade plastic of the syringe barrel 32 and plunger 34, and which does not withstand the temperatures required for heat sterilization of syringes.

More particularly, in accordance with this feature, the material of the sheath 42 has a "deflection temperature" below the "deflection temperature" of the material of the syringe barrel 32 and plunger 34, and below the autoclaving temperatures normally required in medical practice to sterilize hypodermic syringes. Deflection temperature of a plastic material in this regard is understood to mean the temperature at which the material loses virtually all of its strength at very low stress. Thus, at temperatures slightly higher than the deflection temperature, the plastic material deforms, and "melts." Thus, exposing plastic articles to temperatures above their deflection temperature results in serious deformation (melting) of the articles.

The materials from which the sheath 42 is made in accordance with this feature preferably is also reasonably transparent. Acrylic styrene copolymer having a deflection temperature of 230° F. is eminently suitable for this purpose. Other suitable plastic materials include styrene-butadiene (deflect. temp. 158° F.), acrylonitril butadiene styrene (ABS) (deflect. temp. 170° F.), and an ionomer known under the trademark SURLYN of Dupont Corporation (deflect. temp. 129° F.) In this connection, acrylic styrene copolymer, styrene-butadiene and acrylonitril butadiene styrene are preferred In light of the foregoing, if one were to attempt to heat sterilize the hypodermic syringe and needle combination of the present invention for reuse, the sheath 42 would melt and render the combination 30, particularly the needle 38, unusable. The just-described feature clearly reduces even further the potential for abuse of the hypodermic syringe and needle combination of the present invention.

Although the manner of using the first preferred embodiment 30 of the novel hypodermic syringe and needle combination of the present invention is apparent from the foregoing description and drawing figures, for the sake of further clarity and full disclosure, the steps are summarized as follows.

Just before use, the tamper evident wrapping seal (not shown) is removed by a doctor (not shown), nurse (not shown), or patient (not shown) from the hypodermic syringe and needle combination 30 of the invention. Thereafter, the cap 46 is removed from the end 44 of the sheath 42, and the sheath 42 is moved upward on the barrel 32, first by dislodging the boss 52 from the first cavity 54 and thereafter by sliding the boss 52 in the guide channel 48. Just before the boss 52 reaches the end of the guide channel 48, it snaps into the cavity 60, indicating that the sheath 42 has reached its second position relative to the barrel 32 and needle 38. The hypodermic syringe and needle combination 30 is used in this configuration to fill the barrel 32 with a drug or medication (not shown) and to administer the medication (not shown) into the patient (not shown). After administration of the medication, the sheath is moved slightly upward, turned, and thereafter moved downward relative to the barrel 32 by riding the boss 52 in the guide channel 50, until the boss 52 is captured in the third cavity 62. This locks the sheath 42 in its final position adapted for safe disposal of the combination 30. Optionally, just before the combination 30 is discarded and as an added safety feature, the cap 46 may be placed back on the end 44 of the sheath 42.

Apparent advantages of the above-described embodiment 30 include the excellent protection it affords against accidentally wounding the hands of doctors, nurses, or other personnel handling the syringe and needle combination 30, before, and especially after administration of a drug (not shown) to a patient (not shown), and the built-in safeguard against abuse or misuse of the syringe and needle combination.

Referring now to FIGS. 12 through 16, a second preferred embodiment 66 of the invention is shown. The second preferred embodiment 66 is similar in many respects to the above-described first preferred embodiment 30, and is therefore described here in less detail. Thus, the second preferred embodiment 66 of the syringe and needle combination of the invention also includes a sheath 42 which is mounted to the syringe barrel 32 for relative motion thereon.

The sheath 42 of the second preferred embodiment 66 includes, on its upper portion, a plurality of circumferentially and substantially evenly spaced fingers 68. As is best shown on FIG. 12, the fingers 68 are defined by the axially disposed slots 70 located in the upper portion of the sheath 42. Each finger 68 includes an inwardly directed boss or protrusion 52. The barrel 32 of the second preferred embodiment 66 includes two circumferential slots or grooves which bear the reference numerals 72 and 74, respectively.

In the second embodiment 66, the sheath 42 has two principal positions relative to the barrel 32 and needle 38. In the first position, shown on FIG. 13, the bosses 52 of the fingers 68 engage the lower circumferential groove 72, and the needle 38 is protected by the sheath 42. In the second position of the sheath 42, the bosses 52 of the fingers 68 engage the upper circumferential groove 74, and the needle 38 is exposed. After the hypodermic syringe and needle combination of the second preferred embodiment 66 has been used for administering medication, the sheath 42 is again placed into the first position wherein it covers the needle 38.

FIGS. 17 and 18 disclose a third preferred embodiment 76 which is similar in construction to the second embodiment 66, but, after the combination has been used for its intended purpose, permits permanent locking of the sheath 42 in the position where the needle 38 is covered. This is accomplished by providing two circumferential grooves 72 and 78 on the lower portion of the barrel 32. Before use, the camming bosses 52 of the fingers 68 rest in the circumferential groove 72 from which they are removed when the sheath 42 is moved upwardly on the barrel 32 to expose the needle 38. Before the third preferred embodiment 76 is used, additional square bosses 80 of the fingers 68 rest on the barrel 32, as is shown on FIG. 17. After use, the sheath 42 is locked into its position to cover the needle 38 by pushing the sheath 42 on the barrel 32 slightly below its original first position, whereby the square bosses 80 engage and lock into the groove 72, and the camming bosses 52 are simply accommodated in the circumferential groove 78.

FIGS. 19 through 23 disclose yet a fourth preferred embodiment 82 of the hypodermic syringe and needle combination of the present invention. The fourth embodiment 82 is similar in many respects to the first preferred embodiment 30 in that an inwardly directed boss 52 of the sheath 42 is guided in a guide channel 84 to accomplish the hereinafter-described functions. More particularly, in the first position of the sheath 42 it covers and protects the needle 38. In this position, the boss 52 is disposed in a side arm 86 of the guide channel 84. In order to prepare the syringe and needle combination 82 for use, the cap 46 is removed and the sheath 42 is slightly turned relative to the barrel 32 until the boss 52 is located in the main guide channel 84. The sheath 42 is then moved upward on the barrel 32 to expose the needle 38. After administration of a drug (not shown) by the combination 82, the sheath 42 is moved downwardly on the barrel 32, and is thereafter turned so as to guide the boss 52 into the second side arm 88 of the guide channel 84. After a slight upward pull, the boss 52 engages and locks into the cavity 90, thereby locking the sheath 42 into its final position for disposal. In this position the needle 38 is covered by the sheath 42, but for added safety the cap 46 is also replaced on the sheath 42.

What has been described above is a novel hypodermic syringe and needle combination having a movably mounted protective sheath to cover the needle before and after the use of the syringe and needle for administering drugs to patients, or in the course of veterinary medicine, drugs to animals. The novel combination of the present invention offers the advantages of safety, substantially eliminates the dangers of accidental wounding and infection of persons by used needles, and significantly reduces the danger for abuse or misuse of disposable syringes and needles.

Inasmuch as many modifications of the present invention may become readily apparent to those skilled in the art in light of the foregoing disclosure, the scope of the present invention should be interpreted solely from the following claims.

What is claimed is:

1. A combination of a hypodermic needle and syringe of the type which is discardable after a single use, the combination comprising:
    a syringe barrel having a plunger mounted in the barrel;
    a hypodermic needle mounted to the barrel at an end of the barrel which is opposite to the end where the plunger enters the barrel;
    a sheath mounted to the barrel and extending therefrom in a first position to substantially cover the needle and thereby prevent the needle from accidental contact with a foreign object or person during transportation and storage of the combination, the sheath being made of a different plastic material than the barrel and the plunger and which melts at lower temperature than the plastic material of the barrel and plunger, below the temperature customarily used for sterilization by heat, whereby repeated use of the syringe through sterilization can be substantially avoided;
    means incorporated into the barrel and the sheath for permitting movement of the sheath upward on the barrel into a second position wherein the needle is at least partially exposed, for permitting downward movement of the sheath on the barrel into a third position wherein the needle is substantially covered by the sheath, and for substantially irreversibly locking the sheath to the barrel in the third position, whereby the needle is protected when the combination is discarded after normal use.

2. The combination of claim 1 wherein the sheath is tapered at its end remote from the barrel.

3. The combination of claim 1 wherein the sheath includes a removable cover at its end remote from the barrel.

4. The combination of claim 1 wherein the plastic material of the sheath is selected from a group consisting of acrylic styrene copolymer, styrene-butadiene, acrylonitril butadiene styrene and SURLYN.

5. The combination of claim 1 wherein the plastic material of the sheath is selected from a group consisting of acrylic styrene copolymer, styrene-butadiene and acrylonitril butadiene styrene.

6. A combination of a hypodermic needle and syringe of the type which is discardable after a single use, the combination comprising:
    a syringe barrel having a plunger mounted in the barrel;
    a hypodermic needle mounted to the barrel at one end of the barrel which is opposite to the end where the plunger enters the barrel;
    a sheath mounted to be slidable on the barrel between a first position wherein the sheath extends to substantially cover the needle and thereby prevents the needle from accidental contact with a foreign object or person during ordinary shipment and storage of the combination, and at least a second position wherein the sheath is retracted to permit ordinary use of the needle, the sheath being made of a different plastic material than the barrel and the plunger and which melts at lower temperature than the plastic material of the barrel and plunger, below the temperature customarily used for sterilization by heat, whereby repeated use of the syringe through sterilization can be substantially avoided.

7. The combination of claim 6 further comprising means for reversibly locking the sheath in the first position.

8. The combination of claim 6 further comprising means for reversibly locking the sheath in the second position.

9. The combination of claim 6 wherein the plastic material of the sheath is selected from a group consisting of acrylic styrene copolymer, styrene-butadiene, acrylonitril butadiene styrene and SURLYN.

10. The combination of claim 6 wherein the plastic material of the sheath is selected from a group consisting of acrylic styrene copolymer, styrene-butadiene and acrylonitril butadiene styrene.

* * * * *